United States Patent [19]

Hunkeler et al.

[11] 4,405,516
[45] Sep. 20, 1983

[54] BENZODIAZEPINE DERIVATIVES

[75] Inventors: Walter Hunkeler, Magden; Emilio Kyburz, Reinach, both of Switzerland

[73] Assignee: Hoffmann-La Roche Inc., Nutley, N.J.

[21] Appl. No.: 403,843

[22] Filed: Jul. 30, 1982

Related U.S. Application Data

[62] Division of Ser. No. 345,852, Feb. 4, 1982, Pat. No. 4,352,815.

[30] Foreign Application Priority Data

Feb. 27, 1981 [CH] Switzerland .................. 1338/81

[51] Int. Cl.$^3$ ............................................. C07D 434/14
[52] U.S. Cl. ..................... 260/239.3 B; 260/239.3 D; 260/239.3 T; 424/244
[58] Field of Search ................. 260/239.3 D, 239.3 B, 260/239.3 T

[56] References Cited

U.S. PATENT DOCUMENTS 4,352,815 10/1982 Hunkeler et al. .................. 424/273

Primary Examiner—Robert T. Bond
Attorney, Agent, or Firm—Jon S. Saxe; Bernard S. Leon; Frank P. Hoffman

[57] ABSTRACT

There is provided imidazodiazepines of the formula

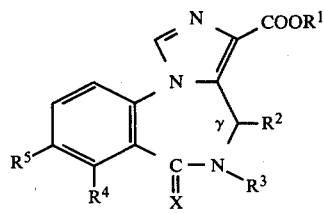

wherein $R^1$ is methyl, ethyl or isopropyl, one of $R^4$ and $R^5$ is hydrogen and the other is nitro or cyano, and either $R^2$ is hydrogen and $R^3$ is hydrogen or lower alkyl or $R^2$ and $R^3$ together are dimethylene, trimethylene or propenylene and the carbon atom denoted as $\gamma$ has the (S)- or (R,S)- configuration, and X is an oxygen or sulphur atom, and their pharmaceutically acceptable acid addition salts. The compounds are useful in the antagonization of the central-depressant muscle relaxant, ataxic, blood pressure-lowering and respiratory-depressant properties of 1,4-benzodiazepines which have tranquillizing activity. They can also be used for suppressing the activities on the central nervous system of 1,4-benzodiazepines used in other fields of indication, for example of schistosomicidally-active 1,4-benzodiazepines. Also provided are methods for making the compounds.

5 Claims, No Drawings

BENZODIAZEPINE DERIVATIVES

This is a division of application Ser. No. 345,852 filed Feb. 4, 1982, now U.S. Pat. No. 4,352,815.

DESCRIPTION OF THE INVENTION

The present invention is concerned with imidazodiazepines. More particularly, the invention is concerned with imidazodiazepines of the formula

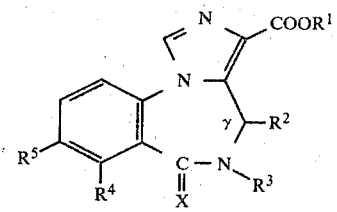

wherein $R^1$ is methyl, ethyl or isopropyl, one of $R^4$ and $R^5$ is hydrogen and the other is nitro or cyano, and either $R^2$ is hydrogen and $R^3$ is hydrogen or lower alkyl or $R^2$ and $R^3$ together are dimethylene, trimethylene or propenylene and the carbon atom denoted as $\gamma$ has the (S)- or (R,S)-configuration and X is an oxygen or sulphur atom, and pharmaceutically acceptable acid addition salts thereof.

Objects of the present invention are compounds of formula I and pharmaceutically acceptable acid addition salts thereof per se and as pharmaceutically active substances, the manufacture of these compounds and intermediates for the manufacture of these compounds, medicaments containing a compound of formula I or a pharmaceutically acceptable acid addition salt thereof and the manufacture of such medicaments.

The term "lower alkyl" denotes saturated hydrocarbon groups, which can be straight-chain or branched-chain, containing at most 7, perferably at most 4, carbon atoms such as methyl, ethyl, n-propyl, isopropyl, n-butyl, s-butyl, t-butyl and the like.

When $R^2$ is hydrogen, then $R^3$ preferably is methyl. When $R^2$ and $R^3$ together are dimethylene or trimethylene, then the carbon atom denoted as $\gamma$ in formula I preferably has the (S)-configuration.

Particularly preferred compounds of formula I are ethyl 5,6-dihydro-5-methyl-7-nitro-6-oxo-4H-imidazo[1,5-a][1,4]benzodiazepine-3-carboxylate and ethyl 7-cyano-5,6-dihydro-5-methyl-6-oxo-4H-imidazo[1,5-a][1,4]benzodiazepine-3-carboxylate.

Other compounds of formula I which are preferred are:

Ethyl 5,6-dihydro-5-methyl-8-nitro-6-oxo-4H-imidazo[1,5-a][1,4]benzodiazepine-3-carboxylate,
ethyl 8-cyano-5,6-dihydro-5-methyl-6-oxo-4H-imidazo[1,5-a][1,4]benzodiazepine-3-carboxylate and
ethyl (S)-(+)-11,12,13,13a-tetrahydro-7-nitro-9-oxo-9H-imidazo[1,5-a]pyrrolo[2,1-c][1,4]benzodiazepine-1-carboxylate.

The imidazodiazepines of formula I and their pharmaceutically acceptable acid addition salts can be manufactured in accordance with the invention by (a) reacting a compound of the formula

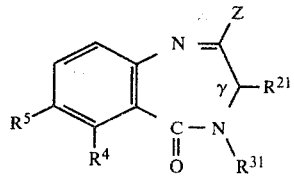

wherein $R^4$ and $R^5$ are as above, Z is a leaving group and either $R^{21}$ is hydrogen and $R^{31}$ is lower alkyl or $R^{21}$ and $R^{31}$ together are dimethylene, trimethylene or propenylene and the carbon atom denoted by $\gamma$ has the (S)- or (R,S)-configuration, in the presence of a base with an isocyanoacetic ester of the formula

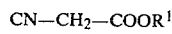

$$CN-CH_2-COOR^1 \qquad III$$

wherein $R^1$ is as above, or (b) replacing the halogen atom in a compound of the formula

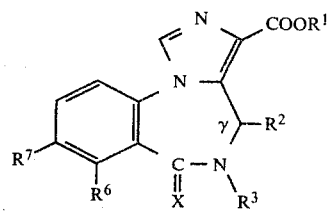

wherein one of $R^6$ and $R^7$ is hydrogen and the other is halogen and $R^1$, $R^2$, $R^3$ and X are as above, by the cyano group, or (c) appropriately substituting a compound of the formula

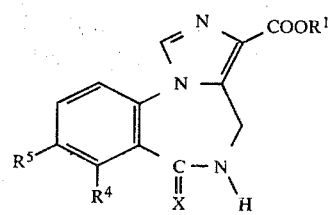

wherein $R^1$, $R^4$, $R^5$ and X are as above,
at the secondary amino group, or (d) cleaving off the protecting group in a compound of the formula

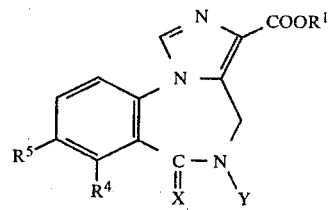

wherein $R^1$, $R^4$, $R^5$ and X are as above and Y is a protecting group, or (e) nitrating a compound of the formula

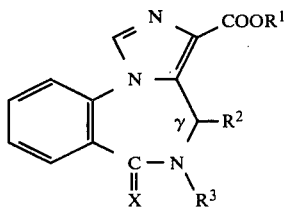

wherein $R^1$, $R^2$, $R^3$ and X are as above, or (f) trans-esterifying a compound of the formula

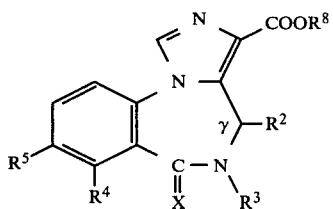

wherein $R^2$, $R^3$, $R^4$, $R^5$ and X are as above and $R^8$ is lower alkyl, or (g) converting the carbonyl group in a compound of the formula

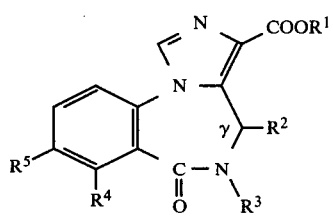

wherein $R^1$, $R^2$, $R^3$, $R^4$ and $R^5$ are as above, into the thiocarbonyl group, and (h) if desired, converting a compound of formula I into a pharmaceutically acceptable acid addition salt.

In accordance with process variant (a), compounds of formula I can be manufactured from compounds of formula II and isocyanoacetic esters of formula III. The leaving group denoted by Z in formula II is, for example, a readily cleavable phosphinyl group, e.g. a group of the formula

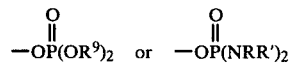

wherein $R^9$ is lower alkyl and R and R' are lower alkyl, allyl, phenyl or substituted phenyl or R and R' together with the nitrogen atom are an unsubstituted or substituted heterocyclic ring with 3–8 members (such as morpholine), a halogen atom, an alkylthio group, an aralkylthio group, a N-nitrosoalkylamino group, an alkoxy group, a mercapto group and the like (when Z is a mercapto group, then the corresponding compound of formula II is the iminothiol form of the corresponding thiolactam). The reaction of a compound of formula II with a compound of formula III is carried out in an inert solvent such as dimethylformamide, hexamethylphosphoric acid triamide, dimethyl sulphoxide, tetrahydrofuran or any other suitable organic solvent and in the presence of a base which is sufficiently strongly basic to form the anion of the isocyanoacetic ester of formula III. Suitable bases are alkali metal alkoxides such as sodium methoxide or potassium t-butoxide, alkali metal hydrides such as sodium hydride, alkali metal amides such as lithium amide or lithium diisopropylamide, tertiary amines such as triethylamine, and the like. The reaction is conveniently carried out at a temperature between about −40° C. and about room temperature.

In accordance with process variant (b), a compound of formula I in which one of $R^4$ and $R^5$ is cyano and the other is hydrogen can be manufactured by replacing the halogen atom in a compound of formula IV by the cyano group. This reaction can be carried out according to methods which are known per se and familiar to any person skilled in the art, for example by treating a halide of formula IV, preferably a bromide or iodide, with copper (I) cyanide in an inert organic solvent. Suitable solvents are, for example, high boiling solvents such as pyridine, dimethylformamide, N-methyl-pyrrolidin-one and the like. The reaction can be carried out in a temperature range of about room temperature to about 200° C. depending on the solvent and halide used.

In accordance with process variant (c), compounds of formula I can be manufactured by appropriately substituting compounds of formula Ia at the secondary amino group in the 5-position. This substitution is carries out according to methods known per se using an agent yielding one of the desired lower alkyl groups; for example, a corresponding organic sulphonic acid alkyl ester (e.g. p-toluene-sulphonic acid methyl ester), a corresponding dialkyl sulphate such as dimethyl sulphate and diethyl sulphate, a corresponding alkyl halide such as methyl iodide, ethyl iodide or ethyl bromide, or the like. The compound of formula Ia is conveniently used in the form of an alkali metal salt; this is conveniently achieved by allowing the reaction to proceed in the presence of a strong base or by converting the compound of formula Ia into an alkali metal salt before the reaction with the alkylating agent. Suitable bases are alkali metal alkoxides such as sodium methoxide or potassium t-butoxide, alkali metal hydrides such as sodium hydride, alkali metal amides such as lithium amide or lithium diisopropylamide, and the like. The reaction is conveniently carried out in the presence of an inert organic solvent. Suitable solvents for this purpose are, for example, dimethylformamide, dimethyl sulphoxide, ethyl acetate, lower alkanols and the like. Many other solvents and also solvent mixtures are also suitable and their choice presents no difficulties to a person skilled in the art. The reaction temperature can be varied within fairly wide limits and generally lies between about room temperature and about the boiling point of the reaction mixture.

In accordance with process variant (d), compounds of formula I can be manufactured by cleaving off the protecting group denoted by Y in compounds of formula V. In this variant there is utilized only protecting groups which can be cleaved off under mild acidic conditions, for example using dilute aqueous mineral acids such as dilute hydrochloric acid or dilute sulphuric acid, trifluoroacetic acid or the like, optionally with the addition of a solubilizer such as tetrahydrofuran, dioxan, acetic acid, N,N-dimethylformamide or the like. The cleavage is conveniently carried out at a temperature beneath about room temperature and the boiling point of the mixture, the latter being preferred. An especially suitable protecting group is the 2,4-dimethoxybenzyl group which is conveniently cleaved off using trifluoroacetic acid, preferably at the boiling point of the mixture.

In accordance with process variant (e), compounds of formula I in which $R^4$ is hydrogen and $R^5$ is nitro can be manufactured by nitrating a compound of formula VI. The nitration can be carried out according to methods which are known per se and familiar to any person skilled in the art. Depending on the reactivity of the compound of formula VI, the nitrating can be carried out using concentrated nitric acid and concentrated sulphuric acid at a temperature of about 0° C. to about 150° C.

In accordance with process variant (f), compounds of formula I can be manufactured by transesterifying a compound of formula VII, i.e. by replacing the alkyl group denoted by $R^8$ in a compound of formula VII by a group $R^1$ whereby, $R^8$ and $R^1$ are different groups. Insofar as $R^8$ in formula VII is methyl, ethyl or isopropyl, the compounds of formula VII fall within formula I hereinbefore. $R^8$ can, of course, also be another lower alkyl group.

This trans-esterfication is carried out in a manner known per se by reacting a compound of formula VII with an alcohol corresponding to the desired group denoted by $R^1$ (i.e. methanol or ethanol or isopropanol) at room temperature or while heating to a temperature of about 25° to 150° C. Preferably, the trans-esterification is carried out in the presence of a base, with potassium cyanide or similar weak bases or the alcoholates corresponding to the desired group denoted by $R^1$ being especially suitable in the present case. As the solvent there is preferably used the alcohol corresponding to the group denoted by $R^1$ in the desired compound of formula I. However, the trans-esterification can also be carried out in an inert organic solvent, for example an aromatic hydrocarbon such as benzene or xylene, an ether such as dioxan, tetrahydrofuran or ethyleneglycol dimethyl ether, dimethylformamide, dimethyl sulphoxide or the like. In this trans-esterification not only can a low boiling alcohol be replaced by a high boiling alcohol, but also a high boiling alcohol can be replaced by a low boiling alcohol.

The trans-esterification can, however, also be carried out readily in several stages; for example, by hydrolyzing a compound of formula VII to the corresponding free carboxylic acid, preparing from this a reactive functional derivative (e.g. an acid chloride or the like) and subsequently reacting this reactive carboxylic acid derivative with the alcohol corresponding to the significance of $R^1$ in Formula I.

In accordance with process variant (g), compounds of formula Ib can be converted into corresponding compounds of formula I by which X is a sulphur atom namely by treatment with a sulphurizing agent, which can be carried out in a manner known per se. For example, the sulphurizing agent can be phosphorus pentasulphide, this being preferably used in excess and the reaction being advantageously carried out in an inert organic solvent such as dioxan, methylene chloride or the like in the presence of triethylamine at a temperature of from about 50° C. up to the reflux temperature of the reaction mixture. Other suitable sulphurizing agents are compounds such as 2,4-bis(p-methoxyphenyl)-1,3,2,4-dithiaphosphetane-2,4-disulphide; such sulphurizing agents being used in approximately the calculated amount and the reaction being carried out in the presence of an inert solvent such as toluene or xylene, conveniently at the reflux temperature of the reaction mixture, or in hexamethylphosphoric acid triamide at a temperature between about 60° and 110° C.

In accordance with process variant (h), compounds of formula I can be converted into pharmaceutically acceptable acid addition salts. The manufacture of such pharmaceutically acceptable acid addition salts is carried out according to generally usual methods. The salts provided by the present invention are salts formed with inorganic acids and with organic acids; for example, hydrochlorides, hydrobromides, sulphates, methanesulphonates, p-toluenesulphonates, oxalates and the like.

The compounds of formula II used as starting materials can be prepared starting from compounds of the formula

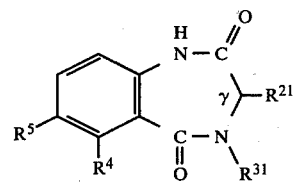

wherein $R^{21}$, $R^{31}$, $R^4$ and $R^5$ are as above
according to methods which are known per se; see, for example, Belgian patent specification Nos. 802 233, 833 249 and 865 653, American patent No. 3,681,341 and J. Org. Chemistry 29, 231 (1964), which are incorporated herein for reference purposes.

Various Examples hereinafter contain detailed information relating to the preparation of compounds of formula II from compounds of formula VIII.

The compounds of formula VIII, in turn, belong to a class of substance known per se and can be prepared readily by any person skilled in the art in analogy to the known members of this class of substance. Thus, the compounds of formula VIII can be prepared, for example, by reacting a corresponding carboxylic acid anhydride of the formula

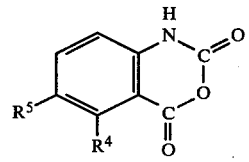

wherein $R^4$ and $R^5$ are as above
with an amino acid of the formula

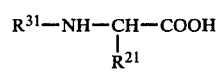

wherein $R^{21}$ and $R^{31}$ are as above

Compounds of formula VIII in which $R^{21}$ is hydrogen and $R^{31}$ is lower alkyl can, however, also be prepared starting from compounds of the formula

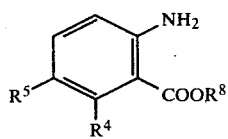
XI wherein $R^4$, $R^5$ and $R^8$ are as above for example by treating such a compound with a reactive derivative of an α-haloacetic acid (e.g. α-chloroacetyl chloride) and reacting the intermediate obtained with a lower alkylamine such as methylamine, ethylamine or the like. There are thus obtained compounds of the formula

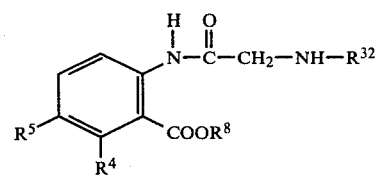
XII wherein $R^4$, $R^5$ and $R^8$ are as above and $R^{32}$ is lower alkyl.

By cyclizing compounds of formula XII there are obtained compounds of formula VIII in which $R^{21}$ is hydrogen and $R^{31}$ is lower alkyl. This cyclization is carried out, for example, by heating a corresponding compound of formula XII for a short time at a temperature of from about 100° to about 300° C.

It is also possible to react a compound of formula XI with a reactive derivative of carboxylic acid of the formula

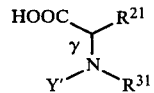
XIII wherein $R^{21}$ and $R^{31}$ are as above and Y' is a protecting group, for example, a carboxylic acid chloride or the like. After removal of the protecting group denoted by Y' from a thus-obtained compound of the formula

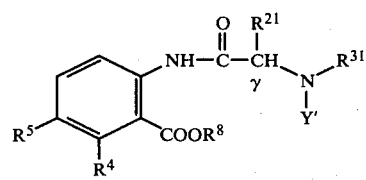
XIV wherein $R^{21}$, $R^{31}$, $R^4$, $R^5$, $R^8$ and Y' are as above, and cyclization, in analogy to the preparation of compounds of formula VIII from compounds of formula XII, there is obtained a compound of formula VIII.

In order to obtain a compound of the formula

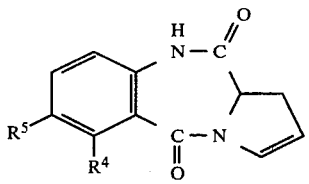
VIIIa wherein $R^4$ and $R^5$ are as above, the leaving group denoted by Z' in a compound of the formula

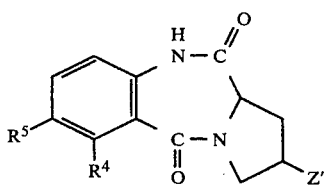
XV wherein $R^4$ and $R^5$ are as above, and Z' is a leaving group, can be eliminated in a manner known per se. Examples of leaving groups are sulphonic acid groups such as methanesulphonyloxy, p-toluenesulphonyloxy or the like, halogen atoms such as chlorine, bromine and iodine, and the like. The cleavage is carried out with a base such as sodium hydride in an inert organic solvent such as dimethylformamide.

Compounds of formula XV can be prepared in analogy to the preparation of compounds of formula VIII from compounds of formulae IX and X or from compounds of formula XIV.

Compounds of formula VIII in which one of $R^4$ and $R^5$ is hydrogen and the other is cyano can, however, also be prepared by replacing the halogen atom in a compound of the formula

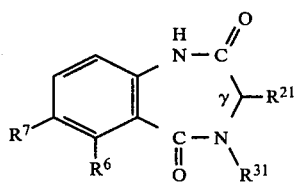
XVI wherein $R^{21}$, $R^{31}$, $R^6$ and $R^7$ are as above, by the cyano group in analogy to process variant (b) described above. Compounds of formula VIII in which $R^4$ is hydrogen and $R^5$ is nitro can also be prepared by nitrating a compound of the formula

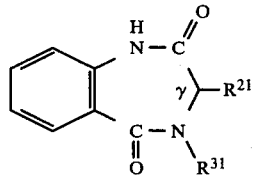
XVII wherein $R^{21}$ and $R^{31}$ are as above, in anaogy to process variant (e) described above. The compounds of formulae XVI and XVII are known or can be readily prepared according to methods known per se; see the method described above for the manufacture of compounds of formula VIII from compounds of formulae IX and X, XII, XIV or XV.

The compounds of formula IV and VI used as starting materials can be prepared in analogy to the processes described above for the manufacture of compounds of formula I; for example, in analogy to process variant (a), starting from compounds of formulae XVI or XVII, or in analogy to process variants (c), (d), (f) or (g) and to the methods described for the preparation of the corresponding starting materials.

Compounds of formula V can be prepared starting from compounds of the formula

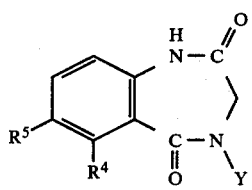

XVIII wherein $R^4$, $R^5$ and Y are as above
in analogy to the methods described above for the manufacture of compounds of formula I in which $R^2$ is hydrogen and $R^3$ is lower alkyl, namely in analogy to process variants (a), (b), (f) and (g) and to the methods described for the preparation of the corresponding starting materials.

Compounds of formula VII in which $R^8$ is other than methyl, ethyl or isopropyl can be prepared in analogy to the methods described above for the manufacture of compounds of formula I in which $R^1$ is methyl, ethyl or isopropyl; namely in analogy to process variants (a), (b), (c), (d), (e), (f) and (g) and to the methods described for the preparation of the corresponding starting materials. Compounds of formula VII in which $R^3$ is other than methyl, ethyl or isopropyl are novel and are likewise an object of the present invention.

The compounds of formulae II and V used as starting materials are also novel and are likewise objects of the present invention.

As mentioned earlier, the compounds of formula I are novel and have extremely valuable pharmacodynamic properties. They exhibit only a low toxicity and it has been shown that they have a pronounced affinity to the central benzodiazepine receptors and are capable of antagonizing the central-depressant, muscle relaxant, ataxic, blood pressure-lowering and respiratory-depressant properties of 1,4-benzodiazepines which have tranquillizing activity.

The affinity of compounds of formula I to the central benzodiazepine receptors was determined according to the method described in Life Science 20, 2101–2110 (1977) and Science 198, 849–851 (1977). According to this method, the inhibition of the binding of tritiated diazepam at the specific benzodiazepine receptors in the cerebral cortex by the respective test substances is ascertained. The $IC_{50}$ ("50% inhibiting concentration") is that concentration of the respective test substance which brings about a 50 percent inhibition of the specific binding of the tritiated diazepam at the specific benzodiazepine receptors in the cerebral cortex.

One of the typical properties of 1,4-benzodiazepines, which have tranquillizing activity, in experimental animals is their pronounced anticonvulsant activity which can be demonstrated, for example, in the known and generally recognized pentetrazole test. This property was used to evaluate the test described hereinafter which permits the determination of compounds which are capable of antagonizing the central properties of 1,4-benzodiazepines which have tranquillizing activity.

In this test, 5 mg/kg (i.p.) of diazepam (i.e. a supramaximal dosage which in the pentetrazole test on more than 900 mice protects all experimental animals from convulsive attacks) were administered to mice 1 hour before the pentetrazole (120 mg/kg i.p.) and the compound to be tested was administered p.o 15 minutes before the pentetrazole. The antagonistic activity of the compounds investigated, i.e. their ability to counteract the activity of the diazepam in the pentetrazole test, is determined by counting the mice which suffer convulsive attacks in this test.

In the following Table there are presented the results which have been obtained with representative members of the class of compound defined by formula I in the test previously described. The $ED_{50}$ value is given for each of the compounds listed in the Table. The $ED_{50}$ is the amount of test compound in mg/kg (p.o.) which counteracts in 50% of the animals the diazepam effect in the above test. Moreover, the Table contains the $IC_{50}$ value (defined above) for all test compounds listed therein.

TABLE

| | Compound of formula I | | | | | | $IC_{50}$ in | $ED_{50}$ in |
|---|---|---|---|---|---|---|---|---|
| $R^1$ | $R^2$ | $R^3$ | Configuration | $R^4$ | $R^5$ | X | nM/l | mg/kg p.o. |
| —CH$_2$CH$_3$ | H | —CH$_3$ | — | —NO$_2$ | H | O | 1.6 | 0.8 |
| —CH$_2$CH$_3$ | H | —CH$_3$ | — | H | —NO$_2$ | O | 20.0 | 3.0 |
| —CH$_2$CH$_3$ | H | —CH$_3$ | — | H | —CN | O | 11.0 | 16.0 |
| —CH$_2$CH$_3$ | H | —CH$_3$ | — | —CN | H | O | 1.3 | 1.12 |
| —CH$_2$CH$_3$ | —(CH$_2$)$_3$— | | (S) | H | —NO$_2$ | O | 90.0 | 12.0 |

As mentioned earlier, the compounds of formula I antagonize the central-depressant, muscle relaxant, ataxic, blood pressure-lowering and respiratory-depressant properties of 1,4-benzodiazepines which have tranquillizing activity. The latter are in widespread use in therapy and are often administered in high dosages, so that the above-mentioned activities can also appear strongly as side-effects. The compounds of formula I can be used as antidotes in the case of intoxications in which excessive intake of 1,4-benzodiazepines which have tranquillizing activity is concerned. They are also suitable for shortening anaesthesia in surgery and in obstetrics induced by 1,4-benzodiazepines which have tranquillizing activity. In the case of neonatals, a possible respiratory depression, which deteriorates upon the administration of 1,4-benzodiazepines which have tranquillizing activity to the mother, can be counteracted. The compounds of formula I can also be used to suppress, in the case of 1,4-benzodiazepines which are used in other fields of indication, the activities on the central nervous system which are undesirable in such fields. Examples of such 1,4-benzodiazepines which can be used in other fields of indication are the schistosomicidally-active 1,4-benzodiazepines described in British patent specifications No. 1 444 529 and 1 474 305 such as (+)-5-(o-chlorophenyl)-1,3-dihydro-3-methyl-7-nitro-2H-1,4-benzodiazepin-2-one.

The compounds of formula I and their pharmaceutically acceptable acid addition salts can be used as medicaments, for example, in the form of pharmaceutical preparations. The pharmaceutical preparations can be administered orally (e.g. in the form of tablets, coated tablets, dragées, hard and soft gelatine capsules, solutions, emulsions or suspensions). The administration can, however, also be carried out rectally (e.g. in the form of suppositories) or parenterally (e.g. in the form of injection solutions).

For the manufacture of tablets, coated tablets, dragées and hard gelatine capsules, the compounds of formula I and their pharmaceutically acceptable acid addition salts can be processed with pharmaceutical inert, inorganic or organic carriers. Examples of such carriers which can be used for tablets, dragées and hard gelatine capsules are lactose, maize starch or derivatives thereof, talc, stearic acid or its salts etc. Suitable carriers for soft gelatine capsules are, for example, vegetable oils, waxes, fats, semi-solid and liquid polyols etc. Suitable carriers for the manufacture of solutions and syrups are, for example, water, polyols, saccharose, invert sugar, glucose and the like. Suitable carriers for injection solutions are, for example, water, alcohols, polyols, glycerine, vegetable oils etc. Suitable carriers for suppositories are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, colouring agents, flavouring agents, salts for varying the osmotic pressure, buffers, coating agents or antioxidants. They can also contain still other therapeutically valuable substances.

As mentioned earlier, compounds of formula I and pharmaceutically acceptable acid addition salts thereof can be used in accordance with the invention in the control or prevention of illnesses, especially in the antagonization of the central-depressants, muscle relaxant, ataxic, blood pressure-lowering and respiratory-depressant properties of 1,4-benzodiazepines which have tranquillizing activity. In particular, compounds of formula I can be used in combination with the schistosomicidally-active compounds mentioned above, for example in combination with (+)-5-(o-chlorophenyl)-1,3-dihydro-3-methyl-7-nitro-2H-1,4-benzodiazepin-2-one, in the control of schistosomiasis. The compounds of formula I or their pharmaceutically acceptable acid addition salts can be administered before, simultaneously with or after the administration or intake of 1,4-benzodiazepines which have tranquillizing activity. If the compound of formula I or a pharmaceutically acceptable acid addition salt thereof is administered simultaneously with the 1,4-benzodiazepine which has tranquillizing activity, then the administration can be as an ad-hoc combination or in the form of a pharmaceutical combination which contains a compound of formula I or a pharmaceutically acceptable acid addition salt thereof and a 1,4-benzodiazepine derivative which has tranquillizing activity; such pharmaceutical combinations are likewise an object of the present invention. The dosage of the compounds of formula I and their pharmaceutically acceptable acid addition salts can vary within wide limits and is, of course, fitted to the individual requirements in each particular case. In general, a daily dosage of about 0.2 mg to about 500 mg should be appropriate.

As mentioned earlier, medicaments containing a compound of formula I or a pharmaceutically acceptable acid addition salt thereof are likewise an object of the present invention as is a process for the manufacture of such medicaments which comprises bringing one or more compounds of formula I or pharmaceutically acceptable acid addition salts thereof and, if desired, one or more other therapeutically valuable substances into a galenical administration form; in this connection reference is again made to the pharmaceutical combinations mentioned above which are likewise an object of the present invention. In particular, pharmaceutical combinations containing a compound of formula I and one of the schistosomicidally-active compounds mentioned above, especially (+)-5-(o-chlorophenyl)-1,3-dihydro-3-methyl-7-nitro-2H-1,4-benzodiazepin-2-one, are an object of the present invention. Such combinations are suitable for the control of schistosomiasis.

In the following Examples, which illustrate the present invention in more detail but in no way are intended to limit its extent, all temperatures are given in degrees Centigrade.

EXAMPLE 1

(a) A solution of 56.5 g of 2-amino-6-nitrobenzoic acid hydrochloride in 200 ml of demineralized water and 200 ml of tetrahydrofuran is cooled to 10° while stirring and treated with phosgene at 10°–30° for 1 hour, a precipitate resulting. The mixture is subsequently diluted with 300 ml of demineralized water and air is conducted through the suspension vigorously for about 3 hours (until the sample is negative for phosgene). The precipitate is filtered off, washed with water and dried in vacuo over phosphorus pentoxide. There is obtained 6-nitroisatoic acid anhydride as beige crystals of m.p. 220°–222° (decomposition).

(b) A mixture of 30.0 g of 6-nitroisatoic acid anhydride, 13.5 g of sarcosine and 100 ml of dimethyl sulphoxide is heated to 100° for 1.5 hours while stirring. After concentration to dryness, the residue is dissolved in 1.0 l of ethyl acetate. The organic phase is washed four times with 50 ml of saturated sodium bicarbonate solution each time and three times with 100 ml of saturated sodium chloride solution each time, the aqueous phases being back-extracted in each case with 800 ml of ethyl acetate. The combined organic extracts are dried over magnesium sulphate and evaporated. From the residue there is obtained, after recrystallization from acetone/hexane, 3,4-dihydro-4-methyl-6-nitro-2H-1,4-benzodiazepine-2,5-(1H)-dione as faint yellowish crystals of m.p. 287°–289°.

(c) A mixture of 2 g (8.5 mmol) of 3,4-dihydro-4-methyl-6-nitro-2H-1,4-benzodiazepine-2,5-(1H)-dione, 20 ml of chloroform (filtered over basic aluminium oxide), 10.30 g (85 mmol) of dimethylaniline and 1.94 g (12.7 mmol) of phosphorus oxychloride is stirred at boiling temperature for 2.5 hours. The clear solution is poured into 6 g of sodium bicarbonate in 60 ml of water and stirred until the evolution of carbon dioxide has finished. The mixture is extracted twice with chloroform. The organic phase is washed with water, dried over magnesium sulphate and evaporated.

Separately, a solution of 1.44 g (12.8 mmol) of potassium t-butylate in 10 ml of dimethylformamide is cooled to about −40° and is treated with 1.44 g (12.7 mmol) of ethyl isocyanoacetate. The solution obtained is treated dropwise at −5° to 0° with a solution of the above iminochloride in dimethylaniline and, after removing the cooling bath, the mixture is stirred for a further 20 minutes. The mixture is neutralized with 1.6 ml of acetic acid, poured into about 200 ml of water and extracted twice with 50 ml of chloroform each time. The organic extracts are washed five times with 100 ml of water each time, dried over magnesium sulphate and evaporated in vacuo.

By chromatography of the crude product on a silica gel column and subsequent recrystallization from ethyl acetate/hexane there is obtained pure ethyl 5,6-dihydro-5-methyl-7-nitro-6-oxo-4H-imidazo[1,5-a][1,4]benzodiazepine-3-carboxylate of m.p. 211.5°–213°.

EXAMPLE 2

(a) A mixture of 8.7 g (0.03 mol) of 6-iodoisatoic acid anhydride, 3.2 g (0.036 mol) of sarcosine and 25 ml of dimethylacetamide is heated to boiling under reflux for 1 hour. After cooling and dilution with water, the mixture is extracted with chloroform. The chloroform extracts are dried and evaporated. After recrystallization of the crude product from methylene chloride/ether, there is obtained 3,4-dihydro-6-iodo-4-methyl-2H-1,4-benzodiazepine-2,5(1H)-dione of melting point 214°–217°.

(b) A mixture of 5.7 g (0.018 mol) of 3,4-dihydro-6-iodo-4-methyl-2H-1,4-benzodiazepine-2,5(1H)-dione, 2.4 g (0.026 mol) of copper (I) cyanide and 60 ml of dimethylformamide is heated to 50° for 45 minutes. After cooling, the mixture is diluted with water and extracted several times with chloroform/isopropanol (4:1). The combined organic extracts are dried over magnesium sulphate and evaporated. The yellow-brown crude product is recrystallized from methanol, there being obtained 6-cyano-3,4-dihydro-4-methyl-2H-1,4-benzodiazepine-2,5(1H)-dione of melting point 253°–256° (decomposition).

(c) A suspension of 0.36 g (0.4 mmol) of sodium hydride (55 percent oil dispersion) in 8 ml of dry dimethylformamide is treated with 1.5 g (7.0 mmol) of 6-cyano-3,4-dihydro-4-methyl-2H-1,4-benzodiazepine-2,5(1H)-dione. After completion of the gas evolution, the mixture is cooled to −35°, treated dropwise with 1.4 ml (8.4 mmol) of diethylchlorophosphate and the mixture is stirred at −35° to −15° for a further 15 minutes.

Separately, a solution of 0.92 g (8.4 mmol) of potassium t-butylate in 3 ml of dry dimethylformamide is cooled in an acetone/dry-ice bath, treated with 1.1 ml (8.4 mmol) of ethyl isocyanoacetate and the mixture obtained is added dropwise to the mixture obtained according to the preceding paragraph. After removing the cooling bath, the mixture is neutralized at 10° with 0.48 ml of glacial acetic acid, poured into 100 ml of water and extracted three times with chloroform. The organic extracts are washed three times with water, dried over magnesium sulphate and evaporated. The crude product is chromatographed on silica gel using chloroform/methanol (9:1) for the elution and subsequently recrystallized from ethyl acetate. There is obtained ethyl 7-cyano-5,6-dihydro-5-methyl-6-oxo-4H-imidazo[1,5-a]benzodiazepine-3-carboxylate of melting point 200°–201°.

EXAMPLE 3

A mixture of 44.75 g (215 mmol) of 6-nitroisatoic acid anhydride, 21.03 g (236 mmol) of sarcosine and 110 ml of dimethyl sulphoxide is stirred at 100° for 1 hour. The brown solution is poured into 600 ml of ice-water. The mixture is extracted with about 300 ml of ethyl acetate. The aqueous phase is extracted a further twice with 100 ml of ethyl acetate each time, the combined organic extracts are washed three times with 80 ml of water each time, dried over magnesium sulphate and evaporated. The residual oil is crystallized from about 200 ml of ethanol and dried at 50° in vacuo. There is obtained 3,4-dihydro-4-methyl-7-nitro-2H-1,4-benzodiazepine-2,5(1H)-dione of melting point 250°–252°. By evaporating the mother liquor and recrystallizing the thus-obtained residue from ethyl acetate there is obtained a further portion of the above dione of melting point 250°–252°.

(b) A suspension, stirred under argon, of 16.0 g (68 mmol) of 3,4-dihydro-4-methyl-7-nitro-2H-1,4-benzodiazepine-2,5(1H)-dione in 100 ml of dimethylformamide is treated with 9.12 g (81.6 mmol) of potassium t-butylate, cooled to −30° C. and treated dropwise at this temperature with 10.5 ml (71.4 mmol) of diethylchlorophosphate. The mixture is stirred at −30° for a further 0.25 hours.

Separately, a solution of 8.36 g (74.8 mmol) of potassium t-butylate in 25 ml of dimethylformamide is cooled in an acetone/dry-ice bath, treated with 8.5 ml (74.8 mmol) of ethyl isocyanoacetate and added dropwise at −30° to −15° to the mixture obtained according to the preceding paragraph. The cooling bath is removed, the mixture is stirred until the temperature has reached 25°, neutralized with about 2 ml of glacial acetic acid, poured into about 400 ml of water and extracted three times with about 150 ml of chloroform each time. The combined chloroform extracts are washed twice with about 80 ml of water each time, dried over magnesium sulphate and evaporated in vacuo.

Purification of the crude product by chromatography on a silica gel column and subsequent recrystallization from ethyl acetate yields ethyl 5,6-dihydro-5-methyl-8-nitro-6-oxo-4H-imidazo[1,5-a]benzodiazepine-3-carboxylate of melting point 197°–199°.

EXAMPLE 4

(a) 300 ml of 89 percent nitric acid are treated portionwise at room temperature over a period of 35 minutes with 94.5 g. (496.8 mmol) of 3,4-dihydro-4-methyl-2H-1,4-benzodiazepine-2,5(1H)-dione. The mixture is stirred at room temperature for 18 hours and poured into 3.5 l of ice-water. The precipitated material is filtered off under suction, washed with water and dried at 70° in vacuo. There is obtained 3,4-dihydro-4-methyl-7-nitro-2H-1,4-benzodiazepine-2,5(1H)-dione of melting point 252°–253°.

(b) In analogy to the details in Example 3(b), from the above dione there is obtained ethyl 5,6-dihydro-5-methyl-8-nitro-6-oxo-4H-imidazo[1,5-a]benzodiazepine-3-carboxylate of melting point 197°–199°.

EXAMPLE 5

(a) 19.0 g (0.10 mol) of 3,4-dihydro-4-2H-1,4-benzodiazepine-2,5(1H)-dione are placed in 100 ml of dry dimethylformamide under an argon atmosphere. 15.5 g (0.12 mol) of potassium t-butylate are added thereto, the temperature rising from 25° to 39°. The mixture is cooled to room temperature and 18.2 g (0.105 mol) of diethylchlorophosphate are added dropwise thereto at between 18°–22°.

Separately, 11.2 g (0.10 mol) of potassium t-butylate are dissolved in 30 ml of dimethylformamide. This solution is cooled to about −50° and treated under argon with 11.3 g (0.10 mol) of ethyl isocyanoacetate. Subsequently, this solution is added dropwise at 18° to 23° while cooling to the mixture obtained according to the preceding paragraph. The mixture is stirred at room temperature for 1 hour, 5 ml of acetic acid are added thereto, then the mixture is poured into 500 ml of water and extracted twice with 200 ml of chloroform each time. The combined chloroform extracts are washed three times with 300 ml of water each time, dried over magnesium sulphate and evaporated. 150 ml of ethyl acetate are added to the oily residue and it is left to crystallize at 0°. The separated crystals are filtered off under suction and washed with cold ethyl acetate, there being obtained ethyl 5,6-dihydro-5-methyl-6-oxo-4H-imidazo[1,5-a][1,4]benzodiazepine-3-carboxylate of melting point 163°–165°. After recrystallization from 50 ml of ethyl acetate, the product has a melting point of 164°–165°.

(b) 2.85 g of ethyl 5,6-dihydro-5-methyl-6-oxo-4H-imidazo[1,5-a][1,4]benzodiazepine-3-carboxylate are dissolved in a mixture of 10 ml of 98 percent nitric acid and 15 ml of 98 percent sulphuric acid and heated to 120° for 2 hours. Subsequently, the mixture obtained is cooled to room temperature, poured onto ice, neutralized with about 25 percent ammonia and extracted with chloroform. The chloroform extracts are dried over magnesium sulphate and evaporated. After recrystallization of the residue from ethyl acetate, there is obtained ethyl 5,6-dihydro-5-methyl-8-nitro-6-oxo-4H-imidazo[1,5-a[1,4]benzodiazepine-3-carboxylate of melting point 197°–198°.

EXAMPLE 6

(a) 130 ml of 89 percent nitric acid are treated portionwise at room temperature over a period of 1.5 hours with 43.0 (199 mmol) of (S)-1,2,3,11a-tetrahydro-5H-pyrrolo[2,1-c][1,4]benzodiazepine-5,11(10H)-dione. The mixture is stirred at room temperature for 18 hours and poured into 1.5 l of ice-water. The precipitated material is filtered off under suction, washed with a large amount of water and dried at 80° in vacuo. There is obtained (S)-(+)-1,2,3,11a-tetrahydro-7-nitro-5H-pyrrolo[2,1-c][1,4]benzodiazepine-5,11(1OH)-dione of melting point 259°–261°.

(b) A solution, cooled to 5°, of 22.0 g (84.2 mmol) of (S)-(+)-1,2,3,11a-tetrahydro-7-nitro-5H-pyrrolo[2,1-c][1,4]benzodiazepine-5,11(1OH)-dione in 100 ml of dimethylformamide is treated with 11.3 g (101 mmol) of potassium t-butylate. 12.6 ml (88.4 mmol) of diethylchlorophosphate are added dropwise at −40° to the dark red solution obtained. The mixture is stirred at −20° to −10° for about a further 20 minutes.

Separately, a solution of 10.4 g (92.6 mmol) of potassium t-butylate in 30 ml of dimethylformamide is cooled in an acetone/dry-ice bath, treated with 10.5 ml (92.6 mmol) of ethyl isocyanoacetate and the mixture obtained is added dropwise at −20° to −10° to the mixture obtained according to the preceding paragraph. The cooling bath is removed, the mixture is stirred until the temperature has reached 20°, neutralized with 3 ml of glacial acetic acid, poured into about 300 ml of ice-water and extracted four times with about 150 ml of chloroform each time. The combined chloroform extracts are washed three times with about 50 ml of saturated sodium chloride solution each time, dried over magnesium sulphate and evaporated.

After purification of the crude product by chromatography on a silica gel column and subsequent recrystallization from ethyl acetate, there is obtained ethyl (S)-(+)-11,12,13,13a-tetrahydro-7-nitro-9-oxo-9H-imidazo[1,5-a]pyrrolo[2,1- c][1,4]benzodiazepine-1-carboxylate of melting point 191°–193°.

EXAMPLE 7

(a) A solution of 21.6 g (0.10 mol) of (S)-(+)-1,2,3,11a-tetrahydro-5H-pyrrolo[2,1-c][1,4]benzodiazepine-5,11(1OH)-dione in 100 ml of dry dimethylformamide is treated under an argon atmosphere with 13.5 g (0.12 mol) of potassium t-butylate, the temperature rising from 24° to 46°. The mixture is cooled to room temperature and 18.2 g (0.105 mol) of diethylchlorophosphate are added dropwise thereto at between 18° to 23°.

Separately, 11.2 g (0.10 mol) of potassium t-butylate are dissolved in 30 ml of dimethylformamide. This solution is cooled to about −50° and treated under argon with 11.3 g (0.10 mol) of ethyl isocyanoacetate. Subsequently, this solution is added dropwise at 18° to 23° while cooling to the mixture obtained according to the preceding paragraph. The mixture is stirred at room temperature for 1 hour, 5 ml of acetic acid are added thereto, then the mixture is poured into 500 ml of water and extracted twice with 200 ml of chloroform each time. The combined chloroform phases are washed three times with 300 ml of water each time, dried over magnesium sulphate and evaporated. 150 ml of acetic acid are added to the oily residue and it is left to crystallize at 0°. The separated crystals are filtered off under suction and washed with cold ethyl acetate, there being obtained ethyl (S)-11,12,13,13a-tetrahydro-9-oxo-9H-imidazo[1,5-a]pyrrolo[2,1-c][1,4]benzodiazepine-1-carboxylate of melting point 196°–197°. The mother liquor is evaporated and the residue is dissolved in 50 ml of ethyl acetate. Therefrom there crystallizes a further portion of the above product; melting point 195°–196°.

(b) A solution of 3.11 g of ethyl (S)-11,12,13,13a-tetrahydro-9-oxo-9H-imidazo[1,5-a]pyrrolo[2,1-c][1,4]benzodiazepine-1-carboxylate in a mixture of 10 ml of 98 percent nitric acid and 15 ml of 98 percent sulphuric acid is heated to 100° for 6 hours. Subsequently, the mixture is cooled to room temperature, poured onto ice, neutralized with about 25 percent ammonia and extracted with chloroform. The chloroform extracts are dried over magnesium sulphate and evaporated. The residue is recrystallized from ethyl acetate and yields ethyl (S)-11,12,13,13a-tetrahydro-7-nitro-9-oxo-9H-imidazo[1,5-a]pyrrolo[2,1-c][1,4]benzodiazepine-1-carboxylate of melting point 193°–194°.

EXAMPLE 8

(a) A mixture of 39.5 g of 5-bromoisatoic acid anhydride, 14.5 g of sarcosine and 150 ml of dimethyl sulphoxide is heated to 100° while stirring. After completion of the gas evolution, the mixture is stirred at 100° for a further 30 minutes and subsequently poured into 900 ml of ice-water. The precipitated crystals are filtered off under suction, washed with water and dried at 50° in vacuo over phosphorus pentoxide. There is obtained 7-bromo-3,4-dihydro-4-methyl-2H-1,4-benzodiazepine-2,5(1H)-dione as light beige crystals. A sample recrystallized from methanol has a melting point of 260°–261°.

(b) 15.0 g of 7-bromo-3,4-dihydro-4-methyl-2H-1,4-benzodiazepine-2,5(1H)-dione and 7.5 g of copper (I) cyanide (freshly prepared) are mixed well in a mortar and heated from 165° to 195° with 7.2 ml of dry pyridine (freshly distilled over potassium hydroxide) under argon over a period of 3 hours. After cooling to 150°, the solid mass is dissolved in about 250 ml of boiling dimethylformamide. The mixture is left to cool, poured into 800 ml of ice-water and extracted three times with 500 ml of chloroform each time. The organic extracts are washed with 250 ml of 2N hydrochloric acid and three times with 500 ml of water each time, dried in the presence of active carbon and evaporated. The residue is dissolved in about 1 l of methanol. The solution is concentrated to a volume of 250 ml, treated with active carbon and cooled to 5°. The precipitated material is filtered off under suction and dried, there being obtained 7-cyano-3,4-dihydro-4-methyl-2H-1,4-benzodiazepine-2,5(1H)-dione as white crystals of melting point 256°–258°.

(c) A solution of 5 g (23 mmol) of 7-cyano-3,4-dihydro-4-methyl-2H-1,4-benzodiazepine-2,5(1H)-dione in 25 ml of dimethylformamide is treated under an argon atmosphere with 0.96 g (25 mmol) of sodium hydride (60 percent oil dispersion) and the mixture is stirred for 1 hour. 4.31 g (25 mmol) of diethylchlorophosphate are added to the suspension obtained at −20° and the mixture is stirred at this temperature for 10 minutes.

Separately, a solution of 2.80 g (25 mmol) of potassium t-butylate in 10 ml of dimethylformamide is cooled in an acetone/dry-ice bath and treated with 2.83 g (25 mol) of ethyl isocyanoacetate. This solution is added dropwise at −10° to −20° to the mixture obtained according to the preceding paragraph. The mixture is stirred without cooling for a further 0.5 hour, neutralized with 2.5 ml of acetic acid, poured into about 250 ml of water and extracted three times with chloroform. The organic extracts are washed five times with water, dried over magnesium sulphate and evaporated. After purification of the crude product by column chromatography on silica gel using ethyl acetate for the elution and subsequent recrystallization from ethyl acetate, there is obtained ethyl 8-cyano-5,6-dihydro-5-methyl-6-oxo-4H-imidazo[1,5-a] [1,4]benzodiazepine-3-carboxylate of melting point 183.5°–184.5°.

Ethyl 5,6-dihydro-5-methyl-7-nitro-6-oxo-4H-imidazo[1,5-a][1,4]benzodiazepine-3-carboxylate (active substance A) can be used as the active substance for the manufacture of pharmaceutical preparations as illustrated in Examples A to G:

EXAMPLE A

Tablets containing the following ingredients are manufactured in the usual manner:

|  | Per tablet |
|---|---|
| Active substance A | 1 mg |
| Lactose | 103 mg |
| Maize starch | 25 mg |
| Microcrystalline cellulose | 70 mg |
| Magnesium stearate | 1 mg |
| Total | 200 mg |

EXAMPLE B

Capsules containing the following ingredients are manufactured:

|  | Per capsule |
|---|---|
| Active substance A | 1 mg |
| Lactose | 164 mg |
| Maize starch | 30 mg |
| Talc | 5 mg |
| Total | 200 mg |

The active substance, lactose and maize starch are firstly mixed in a mixer and then in a comminuting machine. The mixture is returned to the mixer, the talc is added thereto and mixed thoroughly. The mixture is filled by machine into hard gelatine capsules.

EXAMPLE C

Injection solutions containing the following ingredients are manufactured:

|  | Per ml |
|---|---|
| Active substance A | 0.5 mg |
| Benzyl alcohol | 0.015 ml |
| Propyleneglycol | 0.4 ml |
| Ethanol (95 percent) | 0.1 ml |
| Sodium benzoate | 48.8 mg |
| Benzoic acid | 1.2 mg |
| Water for injection q.s. ad | 1.0 ml |

For the manufacture of 10 000 ml of injection solution, 5 g of the active substance are dissolved in 150 ml of benzyl alcohol and 4000 ml of propyleneglycol and 1000 ml of ethanol are added thereto. Then, 12 g of benzoic acid are dissolved in the above mixture and there is added thereto a solution of 488 g of sodium benzoate in 300 ml of water for injection. The solution obtained is made up to a volume of 10 000 ml by adding water for injection, filtered and filled into ampoules of suitable size; the residual volume of the ampoules is filled with nitrogen, the ampoules are sealed and sterilized for 30 minutes in an autoclave at 0.7 atmosphere.

EXAMPLE D

Suppositories containing the following ingredients are manufactured:

|  | Per supp. |
|---|---|
| Active substance A | 0.001 g |
| Cocoa butter (m.p. 36–37°) | 1.255 g |
| Carnauba wax | 0.044 g |
| Total | 1.3 g |

The cocoa butter and carnauba wax are melted in a glass or steel vessel, mixed thoroughly and cooled to 45°. Thereupon, there is added thereto the finely powdered active substance and the mixture is stirred until it is completely dispersed. The mixture is poured into suppository moulds of suitable size, left to cool, the suppositories are then removed from the moulds and packed individually in wax paper or metal foil.

EXAMPLE E

Capsules containing the following ingredients are manufactured:

|  | mg/capsule |
|---|---|
| (+)-5-(o-Chlorophenyl)-1,3-dihydro-3-methyl-7-nitro-2H-2,4-benzodiazepin-2-one (active substance B) | 30.0 |
| Active substance A | 20.0 |
| Lactose (crystalline) | 100.0 |
| Maize starch (white) | 27.5 |

| | mg/capsule |
|---|---|
| Talc | 10.0 |
| Magnesium stearate | 2.5 |
| Total | 190.0 |

The two active substances are mixed well with the adjuvants and 190.0 mg of the mixture are filled into interlocking capsules of suitable size.

EXAMPLE F

Tablets containing the following ingredients are manufactured:

| | mg/tablet |
|---|---|
| (+)-5-(o-Chlorophenyl)-1,3-dihydro-3-methyl-7-nitro-2H-1,4-benzodiazepin-2-one (active substance B) | 30.0 |
| Active substance A | 10.0 |
| Lactose (powdered) | 15.0 |
| Maize starch (white) | 19.5 |
| Povidon K30 | 3.5 |
| Maize starch (white) | 10.0 |
| Magnesium stearate | 2.0 |
| Total | 90.0 |

The two active substances, the powdered lactose and the first portion of white maize starch are mixed and sieved. This mixture is moistened with a solution of the Povidon K30 in water, kneaded, granulated, dried and sieved. The second portion of white maize starch and the magnesium stearate are added to the granulate. After mixing, the mass obtained is pressed to tablets weighing 90 mg.

EXAMPLE G

Tablets containing the following ingredients are manufactured:

| | mg/tablet |
|---|---|
| (+)-5-(o-Chlorophenyl)-1,3-dihydro-3-methyl-7-nitro-2H-1,4-benzodiazepin-2-one (active substance B) | 30 |
| Active substance A | 30 |
| Lactose (powdered) | 22 |
| Maize starch (white) | 22 |
| Povidon K30 | 6 |
| Maize starch (white) | 16 |
| Magnesium stearate | 4 |
| Total | 130 |

The two active substances, the powdered lactose and the first portion of white maize starch are mixed and sieved. This mixture is moistened with a solution of the Povidon K30 in water, kneaded, granulated, dried and sieved. The second portion of white maize starch and the magnesium stearate are added to the granulate. After mixing, the mass obtained is pressed to tablets weighing 130 mg.

What is claimed:

1. A compound of the formula

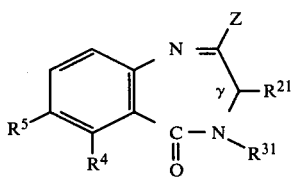

wherein either $R^{21}$ is hydrogen and $R^{31}$ is lower alkyl or $R^{21}$ and $R^{31}$ together are dimethylene, trimethylene or propenylene and the carbon atom denoted as $\gamma$ has the (S)- or (R,S)-configuration, one of $R^4$ and $R^5$ is hydrogen and the other is nitro or cyano and Z is selected from the group consisting of a halogen atom, an alkylthio group, an aralkylthio group, an N-nitrosoalkylamino group, an alkoxy group, a mercapto group, the group

wherein $R^9$ is lower alkyl and the group

wherein R and R' are lower alkyl, alkyl, phenyl or substituted phenyl or R and R' together with the nitrogen atoms are morpholino.

2. The compound of claim 1 wherein $R^{21}$ is hydrogen, $R^{31}$ is methyl and $R^4$ is nitro.

3. The compound of claim 1 wherein $R^{21}$ is hydrogen, $R^{31}$ is methyl and $R^4$ is cyano.

4. The compound of claim 1 wherein $R^{31}$ is methyl.

5. The compound of claim 4 wherein $R^5$ is nitro or cyano.

* * * * *